(12) United States Patent
Roberts et al.

(10) Patent No.: US 10,390,868 B2
(45) Date of Patent: Aug. 27, 2019

(54) FLUID DISPLACEMENT AND PRESSURIZING DEVICES, AND ASSEMBLY THEREOF

(71) Applicant: Atrion Medical Products, Inc., Arab, AL (US)

(72) Inventors: Brian A. Roberts, Owens Cross Roads, AL (US); Rowland W. Kanner, Guntersville, AL (US)

(73) Assignee: ATRION MEDICAL PRODUCTS, INC., Arab ( * ) Notice: Subject to any disclaimer, the term of this patent is extended or adjusted under 35 U.S.C. 154(b) by 357 days.

(21) Appl. No.: 15/014,712

(22) Filed: Feb. 3, 2016

(65) Prior Publication Data

US 2016/0235458 A1 Aug. 18, 2016

Related U.S. Application Data

(60) Provisional application No. 62/116,803, filed on Feb. 16, 2015.

(51) Int. Cl.
*A61B 17/88* (2006.01)
*A61M 25/10* (2013.01)
*A61B 17/00* (2006.01)
*A61B 90/00* (2016.01)

(52) U.S. Cl.
CPC ...... *A61B 17/8825* (2013.01); *A61B 17/8816* (2013.01); *A61B 17/8822* (2013.01); *A61M 25/10182* (2013.11); *A61B 2017/00535* (2013.01); *A61B 2090/063* (2016.02); *A61B 2090/0807* (2016.02)

(58) Field of Classification Search
CPC ........... A61B 17/8822; A61B 17/8825; A61M 25/10182
See application file for complete search history.

(56) References Cited

U.S. PATENT DOCUMENTS

| | | | |
|---|---|---|---|
| 2,695,023 A | 11/1954 | Brown | |
| 3,353,718 A | 11/1967 | McLay | |
| 5,137,514 A * | 8/1992 | Ryan | A61M 25/1018 604/100.01 |
| 5,713,242 A | 2/1998 | Kanner et al. | |

(Continued)

*Primary Examiner* — Olivia C Chang
(74) *Attorney, Agent, or Firm* — Clark Hill PLC; James R. Foley (57) ABSTRACT

A fluid displacement and pressurizing device having a housing and a carrier member. A plunger extends through the carrier member, and plunger engaging structure is retained by the carrier member. The plunger engaging structure is selectively engageable with, and disengageable from, the plunger. The housing and carrier member are configured such that the carrier member is transversely installable in the housing. Preferably, both the carrier member and the plunger engaging structure form a sub-assembly, and the sub-assembly is transversely installable in the housing after having been assembled. By providing that the carrier member is transversely installable as a sub-assembly which includes the plunger engaging structure, the device is easy to assemble, and lends itself well to an automated assembly process. Integral handle and gripping features make control and operation of the devices easier, and allows for torsional operating loads to be resolved without reaching the device body.

13 Claims, 10 Drawing Sheets

(56) References Cited

U.S. PATENT DOCUMENTS

| | | |
|---|---|---|
| 6,796,959 B2 | 9/2004 | Davis et al. |
| 6,938,319 B2 | 9/2005 | Davis et al. |
| 8,191,457 B2 | 6/2012 | Kanner et al. |
| 8,499,681 B2 | 8/2013 | Kanner et al. |
| 2002/0010431 A1 | 1/2002 | Dixon et al. |
| 2008/0077075 A1 | 3/2008 | Moreira et al. |
| 2010/0116360 A1 | 5/2010 | Kanner et al. |
| 2010/0282774 A1 | 11/2010 | Greter et al. |
| 2012/0316507 A1* | 12/2012 | Agard ................ A61B 17/8819 604/187 |

* cited by examiner

FLUID DISPLACEMENT AND PRESSURIZING DEVICES, AND ASSEMBLY THEREOF

RELATED APPLICATION (PRIORITY CLAIM)

This application claims the benefit of U.S. Provisional Application Ser. No. 62/116,803, filed Feb. 16, 2015, which is hereby incorporated herein by reference in its entirety.

BACKGROUND

The present invention generally relates to fluid displacement and pressurizing devices, and methods of assembling such devices.

More specifically, the present invention effectively relates to improvements over the devices and methods of assembly disclosed in U.S. Pat. Nos. 6,796,959; 6,938,319; 8,191,457 and 8,499,681, all of which are incorporated herein by reference in their entirety.

The devices disclosed in those patents utilize a carrier member (see, for example, part number 110 in the '959 and '319 patents) that is inserted longitudinally along the longitudinal axis of the bore of the syringe housing, and then is rotated to engage within the syringe housing and lock against further movement. While the devices disclosed in those patents are reliable for their intended purpose, because the devices are configured such that the carrier member must be longitudinally installed, and then must be rotated to lock the carrier member in place relative to the syringe housing (see, for example, part number 42 in the '959 and '319 patents), before the plunger thread engagement and release mechanism (i.e., the nut member 80 and link members 102, 104 in the '959 and '319 patents) can be installed, none of the devices lend themselves well to an automated method of assembly. Assembly steps to install the carrier member require a longitudinal introduction of the carrier member along the longitudinal axis of the syringe housing, followed by approximately a 90 degree or one-quarter turn rotation to seat and lock the carrier member in place. This installation process is described, for example, at col. 10, lines 3-9, of the '959 patent. This assembly method, which prevents installation of the plunger thread engagement and release mechanism (i.e., the nut member 80 and link members 102, 104 in the '959 and '319 patents) into the carrier member until after the carrier member is seated and locked in the syringe housing, slows the device assembly process.

There is an increasing demand in certain medical fields for disposable syringes made of plastic resin polymers for delivering a large volume of fluid at ultra-high pressure. Some new orthopedic applications, such as expanding inflatable orthopedic nails and bone cement delivery through small cannulas, can require pressures up to 2,700 p.s.i. These extreme pressures require that a user supply a great deal of plunger input torque. In some instances, the required input torque can be twice the force experienced in previous lower pressure applications, which therefore necessitates that the device being used include adequate handles to allow a user to comfortably hold and control the device during pressurization.

Compared to low pressure applications, ultra-high pressure applications present additional challenges when it comes to designs such as that which is disclosed in the previously-identified patents. For example, the extremely high frictional engagement of the heavily loaded nut member (see, for example, part number 80 in the '959 And '319 patents) against the carrier member (i.e., part number 110 in the '959 and '319 patents) combined with the nut member's rotational movement upon release has potential to reverse the quarter-turn rotation used to seat and lock the carrier member (i.e., relative to the syringe housing (i.e., part number 42 in the '959 and '319 patents)). These unlocking forces are transferred directly into the housing through the carrier's retaining mechanism (i.e., part number 172 in the '959 and '319 patents), thereby causing the housing to twist. In order to prevent being overcome by friction induced rotation during unlocking, this retaining mechanism must also be made much larger and more rigid. User input torque required to attain ultra-high pressures using prior art devices, such as that which is disclosed in the previously-identified patents, can also cause the device housing structures to twist in response to torsional loads applied during pressurization. Therefore, these prior art devices must not only have added structure to withstand very high longitudinal plunger loads associated with their pressure capability, but they must also have additional structure to resist torsional reaction from rotational plunger advancement and release of the nut member. Additionally, this high longitudinal loading which transfers directly from the nut member to the carrier member is distributed from the carrier member to the syringe housing by means of a symmetrical pair of bayonet style ears (i.e., part number 172 in the '959 And '319 patents) that, by their very nature (i.e., due to their configuration), can each never be made to engage the housing by more than a quarter of the carrier member's outside diameter. The engagement surface area for these ears is therefore limited, and operation under extreme pressure loading has been shown to exceed the compression strength of the polymers from which the housing and carrier member are formed.

SUMMARY

An object of an embodiment of the present invention is to provide a fluid displacement and pressurizing device which is easy to assemble.

Another object of an embodiment of the present invention is to provide a fluid displacement and pressurizing device which has a configuration such that it lends itself well to being assembled in an automated process.

Still another object of an embodiment of the present invention is to provide a fluid displacement and pressurizing device which allows construction of a relatively inexpensive, highly loaded, ultra-high pressure device within a reasonably compact structure.

Briefly, an embodiment of the present invention provides a fluid displacement and pressurizing device which comprises a housing and a carrier member which is disposed generally in the housing, and which is removable therefrom. A plunger extends through the carrier member, and plunger engaging structure is retained by the carrier member. The plunger engaging structure is selectively engageable with, and disengageable from, the plunger. The housing and carrier member are configured such that the carrier member is transversely installable in the housing, rather than being installable along a longitudinal axis of the housing. Preferably, both the carrier member and the plunger engaging structure form a sub-assembly, and the sub-assembly is transversely installable in the housing after having been assembled. By providing that the carrier member is transversely installable as a sub-assembly which includes the plunger engaging structure, the device is easy to assemble, and the device lends itself well to an automated assembly process.

BRIEF DESCRIPTION OF THE DRAWINGS

The organization and manner of the structure and operation of the invention, together with further objects and advantages thereof, may best be understood by reference to the following description taken in connection with the accompanying drawings wherein like reference numerals identify like elements in which:

FIGS. 4 and 5 are cross-sectional views of the fluid displacement and pressurizing device shown in FIGS. 1-2, taken along line A-A of FIG. 1, showing the device in two different states;

DESCRIPTION OF ILLUSTRATED EMBODIMENTS

While this invention may be susceptible to embodiment in different forms, there are shown in the drawings and will be described herein in detail, specific embodiments with the understanding that the present disclosure is to be considered an exemplification of the principles of the invention, and is not intended to limit the invention to that as illustrated.

Figure 1:
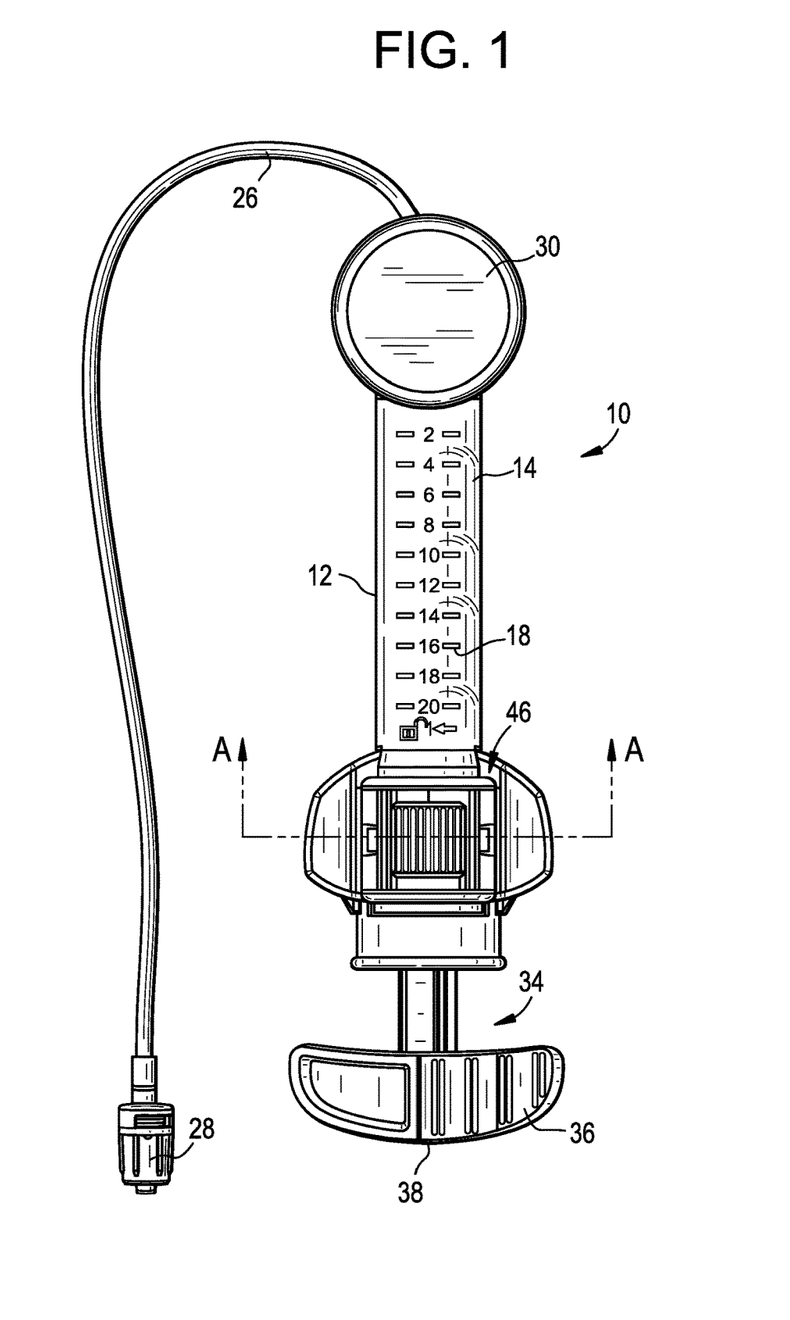
FIG. 1 is a top view of a fluid displacement and pressurizing device, specifically a high volume, ultra-high pressure inflation device, which is in accordance with a first embodiment of the present invention.
Figure 6:
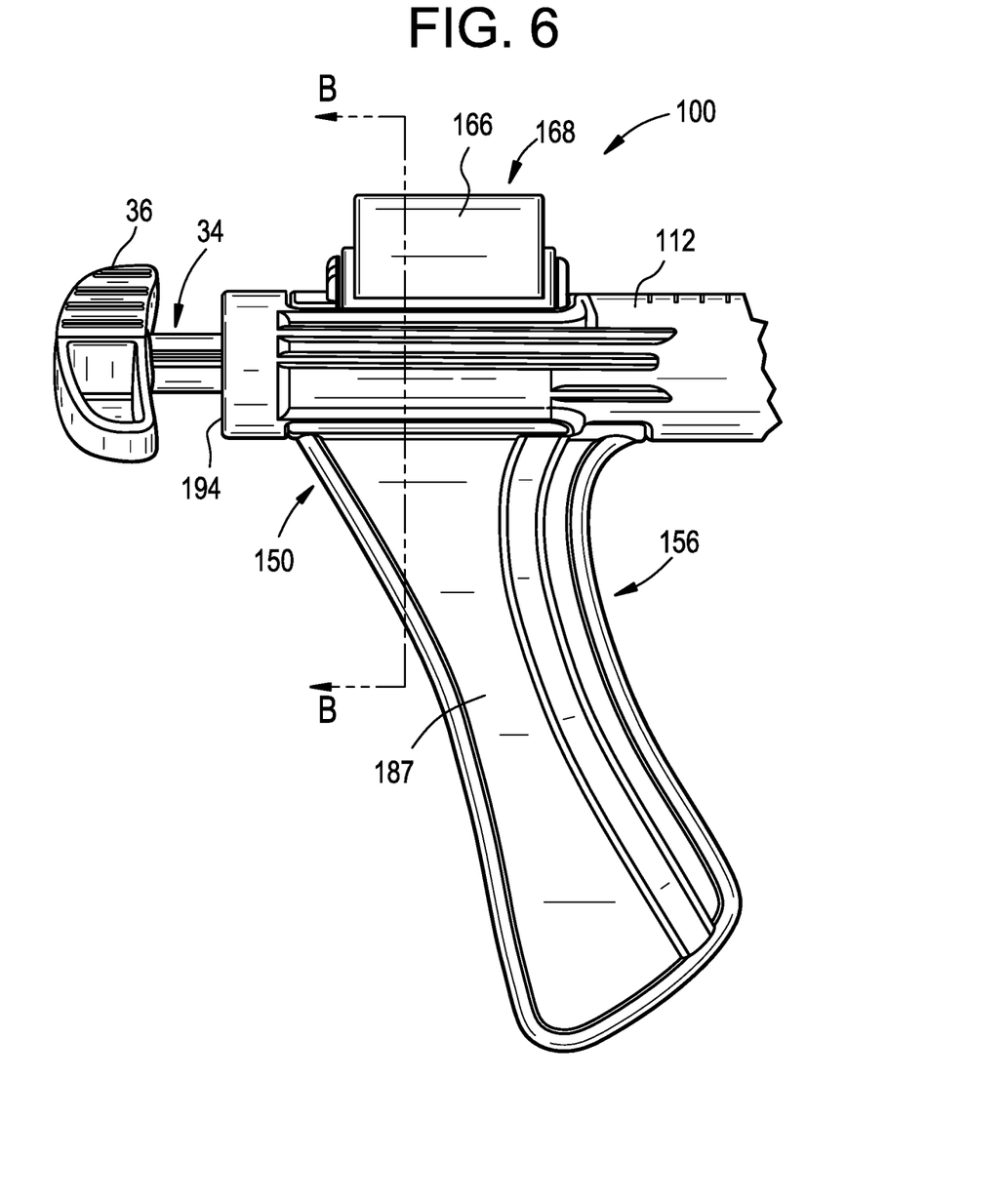
FIG. 6 is a side view of a portion of a fluid displacement and pressurizing device, specifically an ultra-high pressure orthopedic cement delivery device, which is in accordance with a second embodiment of the present invention.

FIGS. 1 and 6 illustrate fluid displacement and pressurizing devices, each of which is in accordance with an embodiment of the present invention. Specifically, FIG. 1 illustrates a high volume, ultra-high pressure inflation device (i.e., an inflator) 10, and FIG. 6 illustrates an ultra-high pressure orthopedic cement delivery device 100. Still other embodiments are entirely possible while still staying very much within the scope of the present invention, but these two specific embodiments are shown for exemplary purposes.

As will be described more fully hereinbelow, both embodiments are easy to assemble, lend themselves well to an automated assembly process, and allow construction of a relatively inexpensive, highly loaded, ultra-high pressure device within a reasonably compact structure. The device 10 illustrated in FIG. 1 will first be described in detail, and then the device 100 illustrated in FIG. 6 will be described, basically emphasizing the differences.

Figure 2:
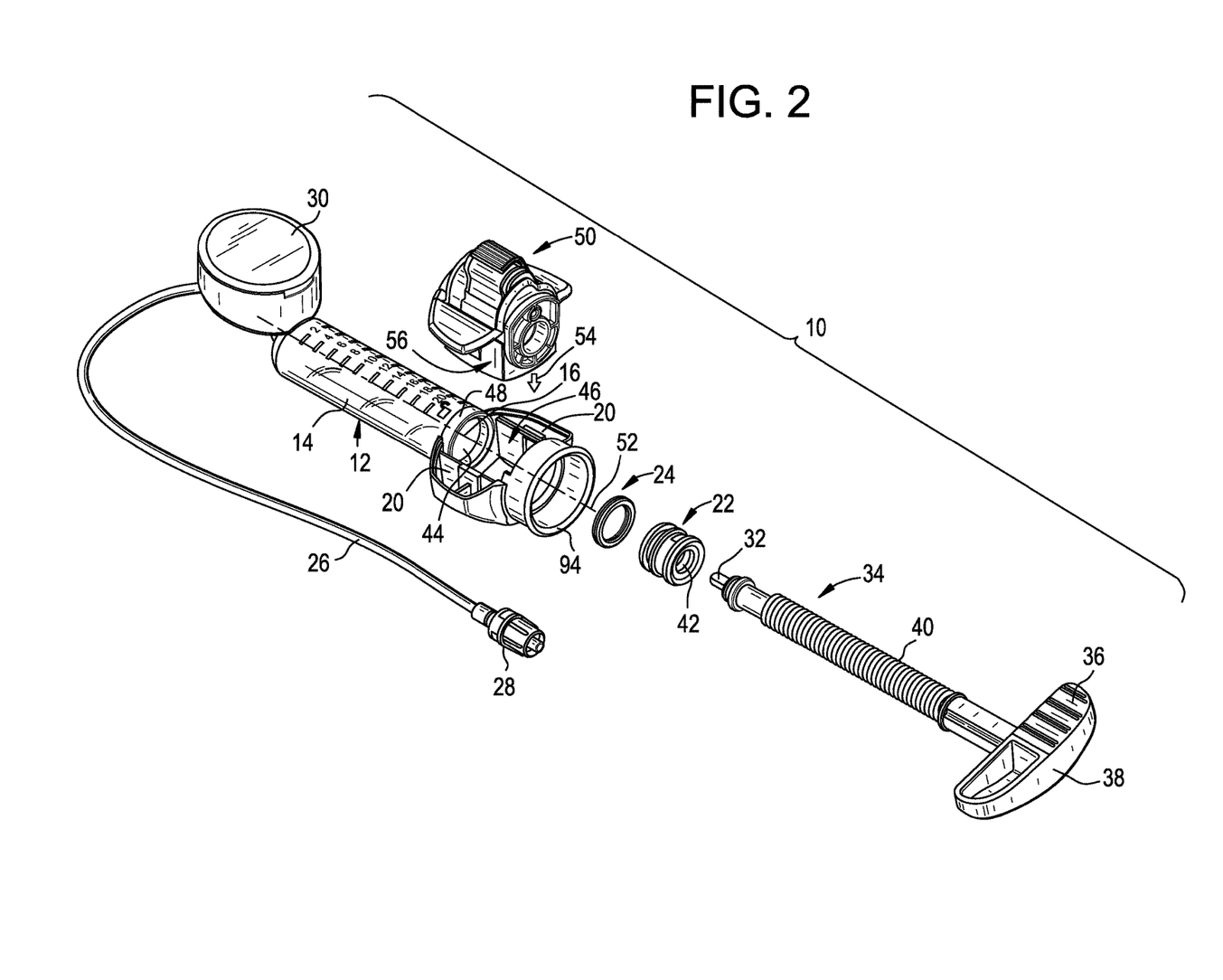
FIG. 2 is an exploded perspective view of the fluid displacement and pressurizing device shown in FIG. 1.

The device 10 illustrated in FIG. 1 is a high volume, ultra-high pressure inflation device (i.e., an inflator). The device 10 comprises a generally cylindrical syringe housing body 12 which provides a barrel 14 having a fluid displacement chamber 16 therein. Preferably, the housing 12 is transparent thereby facilitating the viewing of fluid in the fluid displacement chamber 16 during fluid aspiration or dispensing. The housing is preferably formed of plastic, and may be molded from polycarbonate or another type of resin. The housing preferably has volumetric indicia 18 thereon, so that a user can readily determine the volume of fluid contained in the fluid displacement chamber 16. As shown in FIG. 2, preferably handle portions 20 are provided on sides of the housing 12.

A piston 22 is slidably displaceable within the fluid displacement chamber 16 (i.e., in the housing). A shown in FIG. 2, a sealing member 24, such as a quad ring, is disposed on the piston 22. A lubricant may be used to place the sealing member 24 on the piston 22. The sealing member 24 is configured for pressure retention and the prevention of leakage of fluid past the piston 22 in the fluid displacement chamber 16. As shown in FIGS. 1 and 2, the housing 12 is configured to be connected to a fluid delivery hose 26, and the hose 26 may be connected, and its opposite end, to a connector 28, such as a Luer connector, which is connectable to balloon catheter structure (not shown), a fluid supply reservoir (not shown), or some other structure depending on the application. Preferably, the housing 12 is configured to engage a pressure gauge assembly 30, such that the fluid pressure is displayable.

As shown in FIG. 2, preferably the piston 22 mounts on an unthreaded pilot nose end 32 of a plunger 34. The plunger 34 preferably has a handle 36 at its end 38, opposite the unthreaded pilot nose end 32. Between the handle 36 and the pilot nose end 32 is a thread 40, such that the plunger 34 can be regarded as a threaded screw plunger. The pilot nose end 32 may be configured to freely rotate in a central journal cavity 42 of the piston 22 or lock to prevent free rotation. Specifically, the piston 22 is preferably mounted on the pilot nose end 32 of the plunger 34 in a snap-action, interference coupling which prevents the pilot nose end 32 from readily withdrawing or backing out of the central journal cavity 42 of the piston 22 when the threaded screw plunger is retracted (i.e., using the handle 36) to aspirate fluid into the fluid displacement chamber 16. Preferably, the coupling mechanism between the piston 22 and the plunger 34 is configured to provide a keyed engagement which prevents independent rotation of the two parts from one another while still allowing both parts to be lockingly coupled in a loose enough manner such that each can establish its own alignment within the structure—i.e., piston 22 in alignment with bore, and plunger 34 in alignment with bore and half nut 58. Alternatively, the plunger 34 can be locked to the piston 22 so that both rotate together. This would allow the user to hold the device 10 by its plunger 34 (i.e., by the handle 36), and not have the device 10 rotate out of position relative to the plunger's orientation.

The housing 12 preferably includes a carrier receptacle 46, such as on its top surface 48, for receiving a carrier sub-assembly 50, wherein the carrier sub-assembly 50 is installable relative to the housing 12 in a direction which is traverse to a longitudinal axis 52 of the housing 12. This direction of installation of the carrier sub-assembly 50 relative to the housing 12 is indicated in FIG. 2 with arrow 54.

Figure 3:
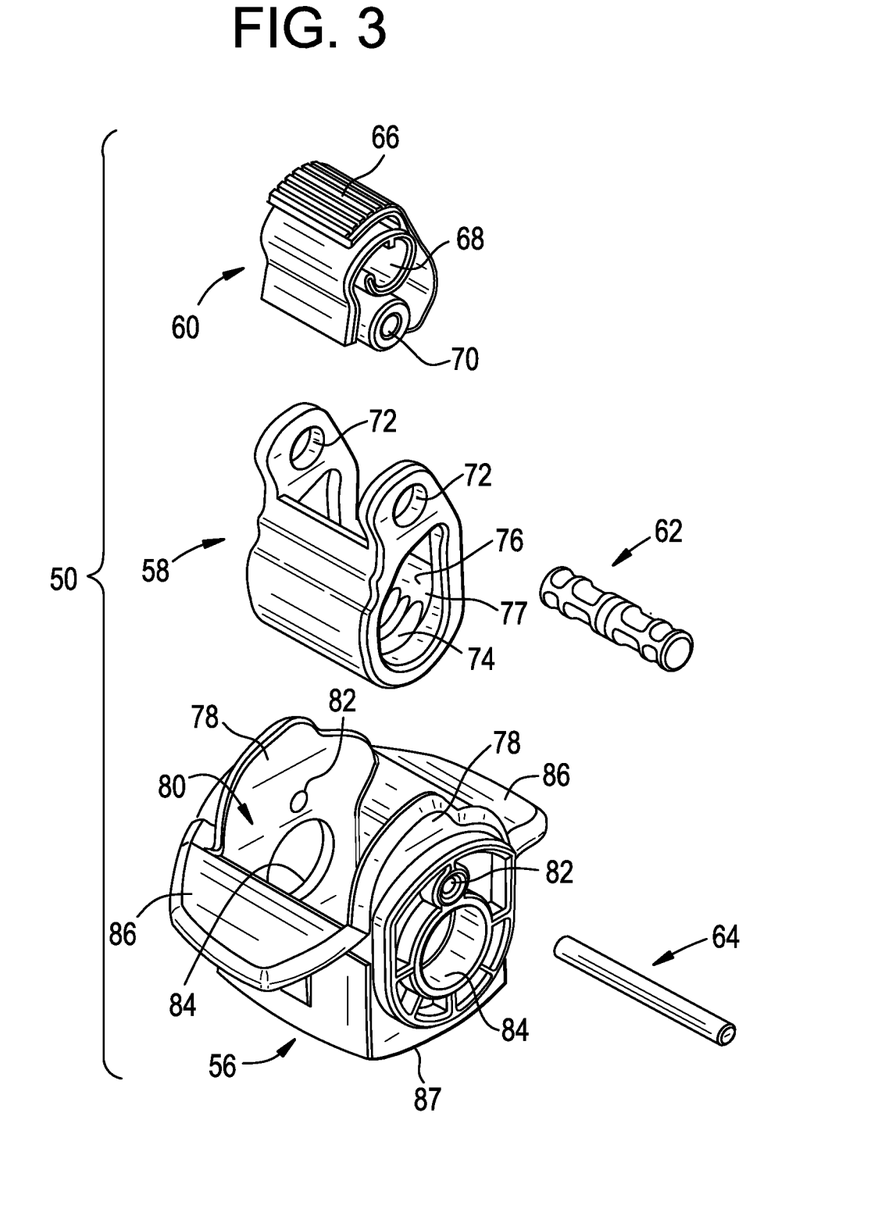
FIG. 3 is an exploded perspective view of a carrier sub-assembly of the fluid displacement and pressurizing device shown in FIGS. 1 and 2.

The preferred components of the carrier sub-assembly 50 can best be seen in FIG. 3, which provides an exploded view of the carrier sub-assembly 50. As shown in FIG. 3, the carrier sub-assembly 50 preferably comprises a carrier member 56, a plunger engaging member such as a nut member or specifically a half nut 58, and an actuating lever-link member 60. The actuating lever-link member 60 is coupled to the half nut 58 via a first pivot pin 62, and is coupled to the carrier member 56 via a second pivot pin 64. All the components may be formed of plastic, but the second pivot pin 64 may instead be formed of metal.

Preferably, the actuating lever-link 60 has a control surface 66 which is configured to be engaged by a user of the device 10. The actuating lever-link 60 also preferably provides a receptacle 68 for receiving the first pivot pin 62, as well as a bearing 70 for receiving the second pivot pin 64. Preferably, the half nut 58 provides bearings 72 for receiving the first pivot pin 62, thread segments 74 on its inner surface 76 for selective engagement with the thread 40 on the plunger 34, and an opening 77 through which the plunger 34 extends once the device 10 is fully assembled. The actuating lever-link member 60 is coupled to the half nut 58 via the first pivot pin 62. Specifically, the first pivot pin 62 extends through the receptacle 68 in the actuating lever-link 60, and is retained proximate each of its ends by the bearings 72 of the half nut 58.

Preferably, the carrier member 56 has spaced-apart walls 78 which define a pocket 80 for receiving the half nut 58 and the actuating lever-link member 60 (i.e., after the half nut 58 and the actuating lever-link member 60 have been coupled together using the first pivot pin 62). The carrier member 56 also includes receptacles 82 for receiving the second pivot pin 64, openings 84 which define a plunger passageway, and handle portions or surfaces 86, 87. The half nut 58 and actuating lever-link member 60 (after having been coupled together using the first pivot pin 62) are coupled to the carrier member 56 via the second pivot pin 64. Specifically, the second pivot pin 64 extends through the bearing 70 in the actuating lever-link member 60, and is retained at each of its ends by the receptacles 82 in the carrier member 56.

Figure 4:
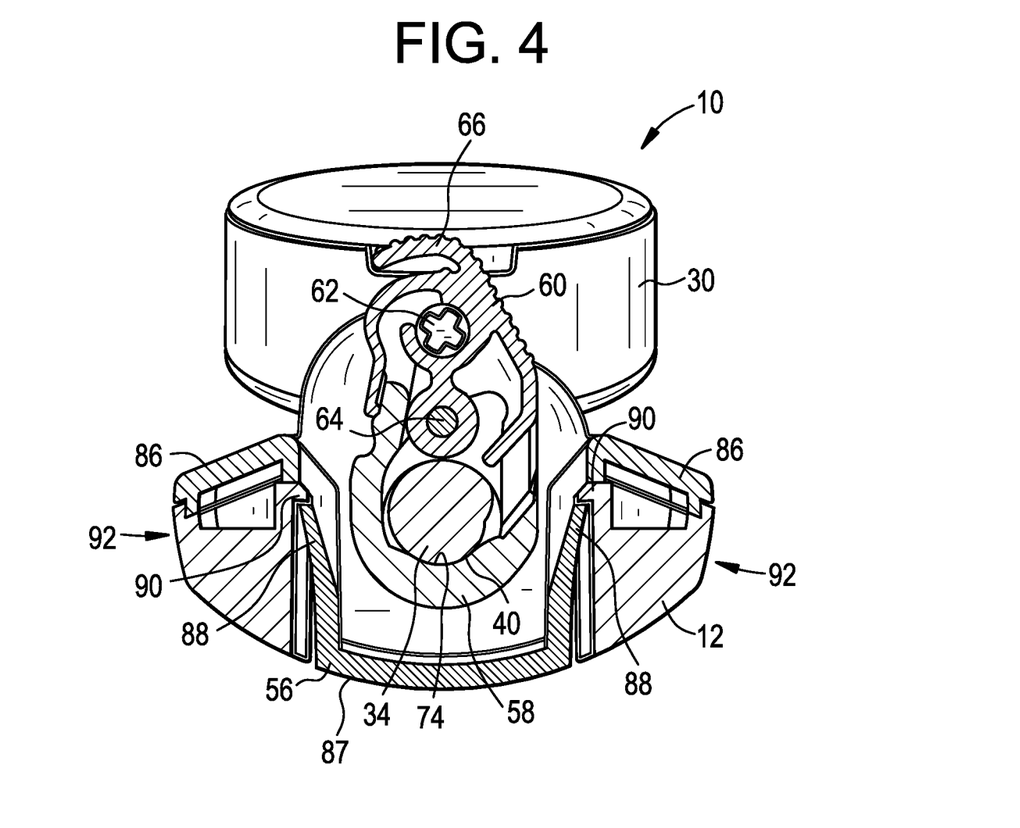
Figure 5:
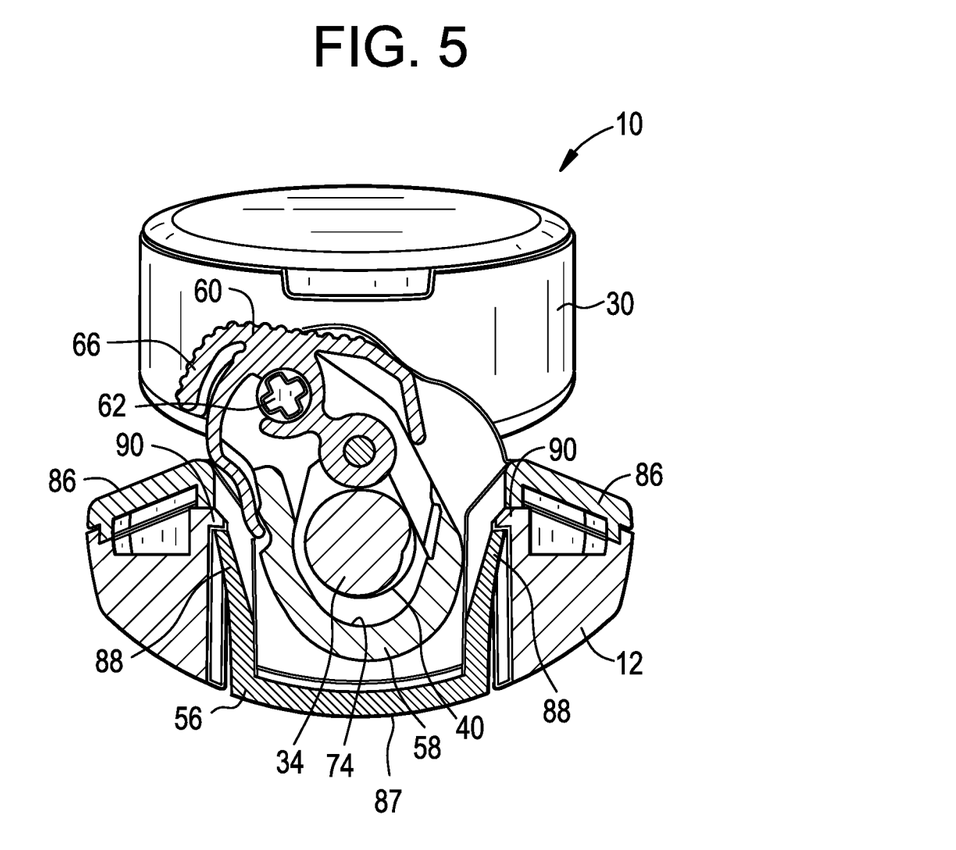
FIG. 5 is a view much like FIG. 4, but showing the device in the unlocked position.

Preferably, the housing 12 and carrier member 56 are configured such that the carrier member 56 snaps in place in the carrier receptacle 46. For example, as shown in FIGS. 4 and 5, the carrier member 56 may comprise deflectable latch elements 88 which engage corresponding striker bar elements 90 which are provided in the housing 12, proximate the carrier receptacle 46, thereby securing the carrier member 56 in the housing 12.

With regard to the structure and function of the half nut and the actuating link-lever, such as when the control surface of the actuating link-lever is pressed or released, or when the handle of the plunger is pushed, pulled or rotated, this need not be explained in extreme detail herein, as that detail is fully explained in the patents previously-identified herein.

With regard to assembly of the device 10 shown in FIGS. 1 and 2, first the carrier sub-assembly 50 is assembled, and then the carrier sub-assembly 50 is installed in the carrier receptacle 46 in the housing 12. To assemble the carrier sub-assembly 50, first the actuating lever-link member 60 is inserted into the half nut 58, and then the first pivot pin 62 is inserted into either one of the bearings 72 in the half nut 58, through the receptacle 68 in the lever-link member 60, and into the other bearing 72 in the half nut 58. This assembly is then inserted into the pocket 80 in the carrier member 56, aligning the bearing 70 of the actuating lever-link 60 with the receptacles 82 in the walls 78 of the carrier member 56. The second pivot pin 64 is then inserted into either one of the receptacles 82, through the bearing 70 in the actuating lever-link 60, and into the other receptacle 82, thereby securing all parts of the carrier sub-assembly 50 into working alignment.

Either before or after assembling the carrier sub-assembly 50, the piston 22 (along with the sealing member 24 thereon) is inserted into the barrel 14 of the housing (into chamber 16 as shown in FIG. 2), thereby causing the sealing member 24 to seal with the internal wall 44 in the barrel 14 of the housing 12.

Regardless, after the piston 22 has been installed in the barrel 14, and after the carrier sub-assembly 50 has been assembled, the carrier sub-assembly 50 is then installed into the carrier receptacle 46 in the housing. This installation is performed in a direction which is traverse to the longitudinal axis 52 of the housing 12 (the direction of installation is illustrated in FIG. 2 using arrow 54), causing the deflectable latch elements 88 on the carrier member 56 to slide past and snap into retaining engagement with the striker bar elements 90 which are provided in the housing 12 (see FIGS. 4 and 5), thereby securing the carrier member sub-assembly 50 in the housing 12.

As shown in FIGS. 4 and 5, once the carrier sub-assembly 50 is installed, the handle portions 86 on the carrier effectively mate with the handle portions 20 on the housing 12, thereby together defining handles 92 which are engaged by the user during operation of the device 10. Furthermore, handle surface 87 effectively closes off the bottom of the carrier receptacle 46, and becomes a handle surface for cradling and supporting the device 10 in the user's hand. If necessary, the entire surface area defined by the rear wall of carrier receptacle 46 may be utilized to receive load from carrier member 56.

The carrier member 56 is configured such that the handle portions 86 isolate torque reaction to the carrier member 56 itself and prevents torsional loads from reaching the device housing 12. These integral handle portions 86 (along with surface 87) serve as the main gripping feature for holding the device 10 and resisting torsional inputs during use. Additionally, unlike the devices disclosed in the previously-identified patents, the carrier member 56 preferably does not rely on bayonet type ears of limited surface area to transfer its load to the housing 12. Instead, the carrier member 56 distributes its load to the housing 12 over a much larger contact area which prevents exceeding the strengths of the polymers that comprise the carrier member 56 and the housing 12.

After the carrier sub-assembly 50 is installed relative to the housing 12, the end 32 of the plunger 34 is securably engaged with the piston 22. To do this, the control surface 66 of the actuating link-lever 60 is pressed which causes the half nut 58 to de-actuate and shift, thereby effectively clearing a passageway for the end 32 of the plunger 34 to access the piston 22. To engage the end 32 of the plunger 34 with the piston 22, while the control surface 66 is being pressed, the end 32 of the plunger 34 is inserted into the end 94 of the housing 12 (see FIG. 2), into the one receptacle 84 in the carrier member 56 (see FIG. 3), pushed along the opening 77 in the half nut 58, through the other receptacle 84 in the carrier member 56, and into secure mating engagement with the piston 22 which is in the barrel 14. Thereafter, the control surface 66 can be released, causing the half nut 58 to pivot into threaded engagement with the plunger 34. At this point (assuming the hose 26 and the gauge 30 are in place), the device 10 is ready for operation.

With regard to operation of the device 10 after it has been assembled, user interactions with both the control surface 66 and the handle 36 of the plunger 34, both regard to macro movement and micro movement of the plunger 34, are disclosed in detail the previously-identified patents, and need not be repeated in extreme detail here. That being said, generally speaking, the actuating lever-link 60 is configured such that the actuating lever-link 60 biases the half nut 58 into threaded engagement with the thread 40 of the plunger 34 (see FIG. 4). At this time, the handle 36 of the plunger 34 is rotatable to cause micro-movement of the plunger 34 (and the piston 22 thereon), via threadable interaction with the thread segments 74 on the half nut 58. Pressing the control surface 66 of the actuating lever-link 60 causes the half nut 58 to disengage from the thread 40 on the plunger 34 (see FIG. 5), thereby allowing macro-movement of the plunger 34 (and the piston 22 thereon) by pushing or pulling on the handle 36.

Figure 7:
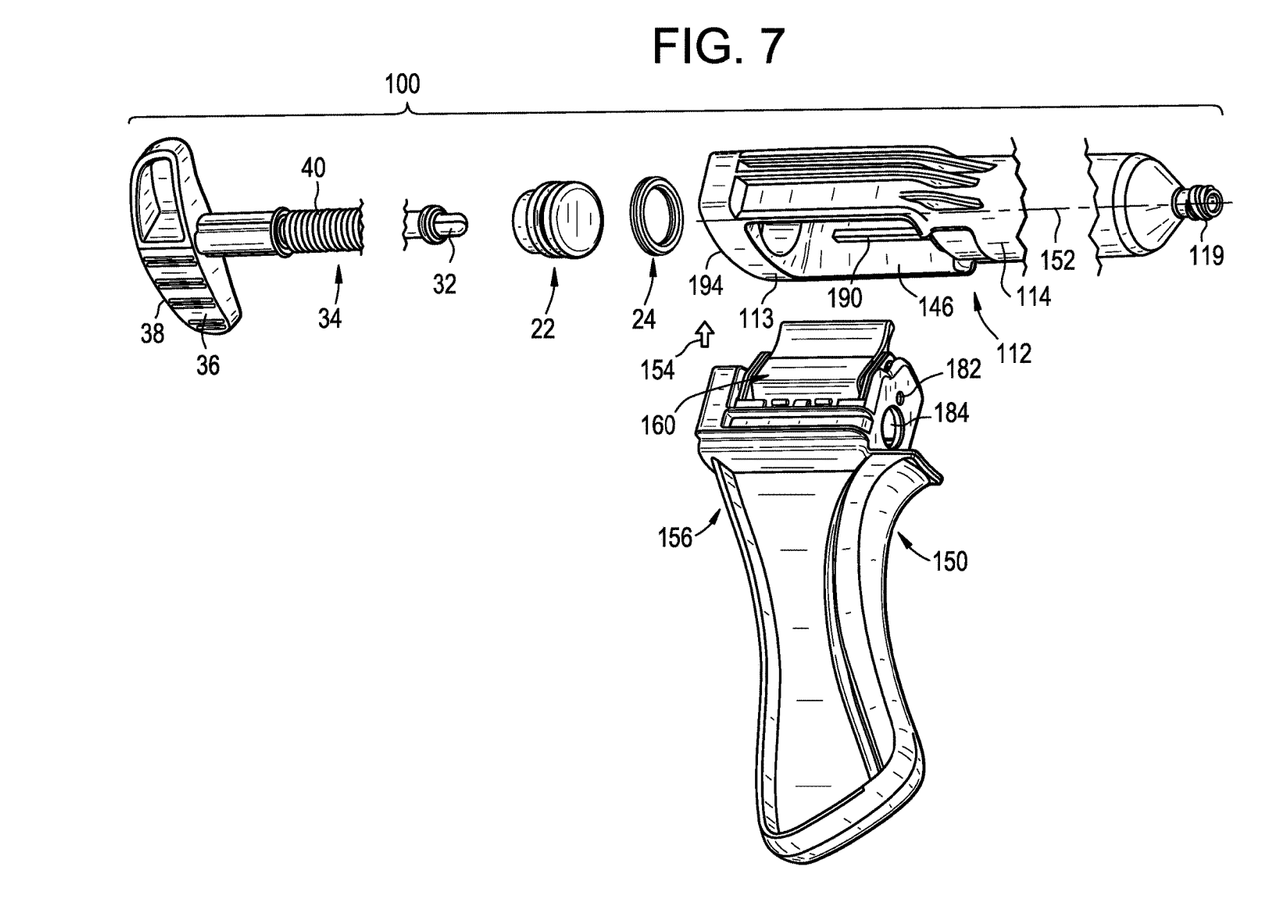
FIG. 7 is an exploded perspective view of that which is shown in FIG. 6.

While the device 10 shown in FIG. 1 differs from the device 100 shown in FIG. 6 in that the device 10 shown in FIGS. 1 and 2 is a high volume, ultra-high pressure inflation device (i.e., an inflator), while the device 100 shown in FIGS. 6 and 7 is an orthopedic cement delivery device, both devices include a carrier sub-assembly that gets installed (after being assembled) in the housing, in a direction which is transverse to a longitudinal axis of the housing.

The device 100 shown in FIG. 6 will now be described. FIG. 7 provides an exploded view thereof. As shown in FIG. 7, much like the device shown in FIGS. 1 and 2 (previously described), the device 100 shown in FIGS. 6 and 7 includes a piston 22, a sealing member 24, and a plunger 34. The plunger 34 has a thread 40 thereon, a handle 36 at one end 38, and a pilot nose end 32 for engaging the piston 22 at the opposite end.

The housing 112 of the device 100 shown in FIGS. 6 and 7 is somewhat different than the housing 12 of the device shown in FIGS. 1 and 2 in that the housing 112 is configured to receive the carrier sub-assembly 150 from the bottom 113 of the housing 112 rather than the top. Regardless, the carrier sub-assembly 150 is configured to be assembled, and then snapped in place relative to the housing 112, in a carrier receptacle 146 in the housing 112, in a direction (indicated with arrow 154 in FIG. 7) which is traverse to a longitudinal axis 152 of the housing 112. The housing 112 includes a barrel 114, and an outlet port 119 proximate its end.

Figure 8:
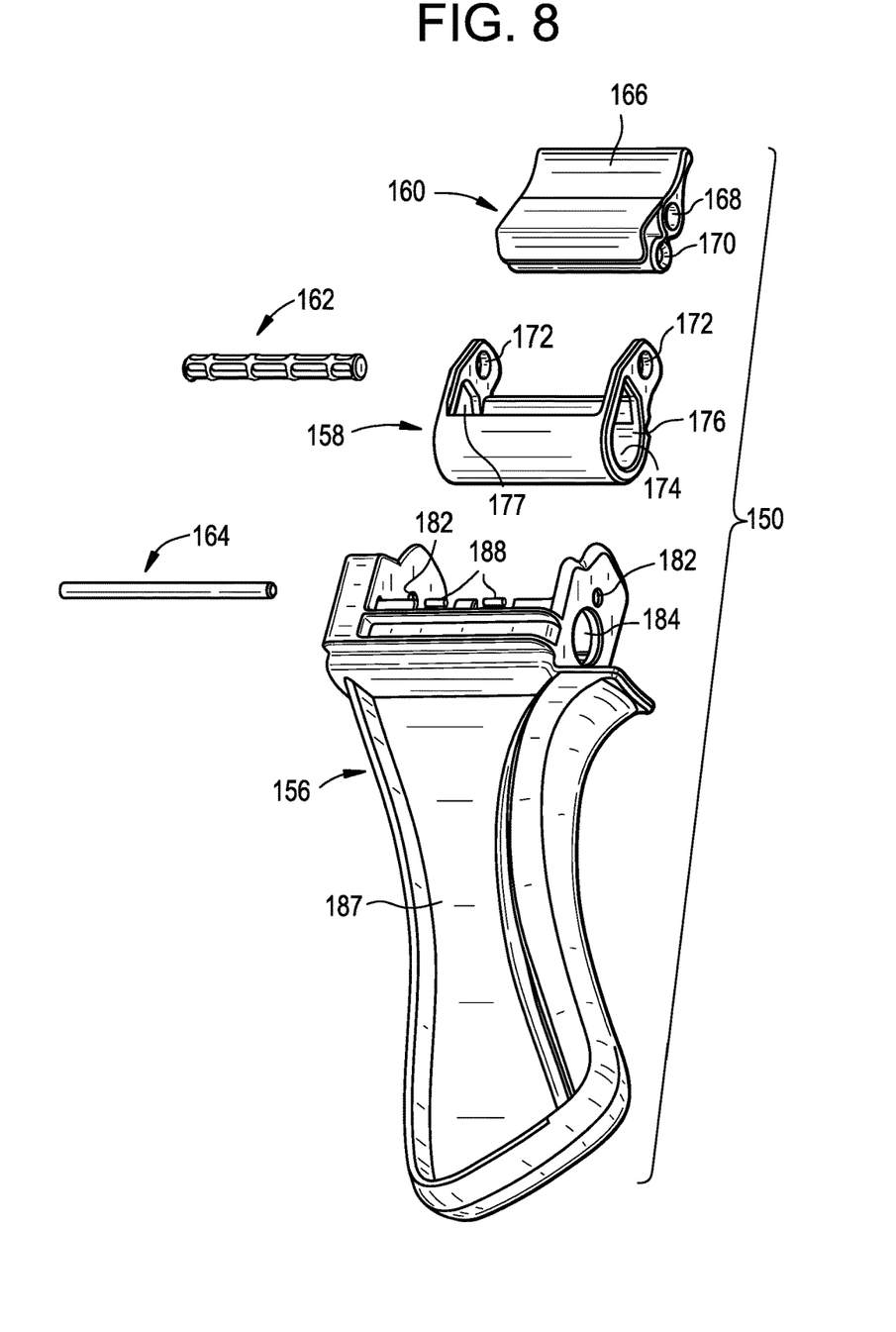
FIG. 8 is an exploded perspective view of a carrier sub-assembly of the fluid displacement and pressurizing device shown in FIGS. 6 and 7.
Figure 9:
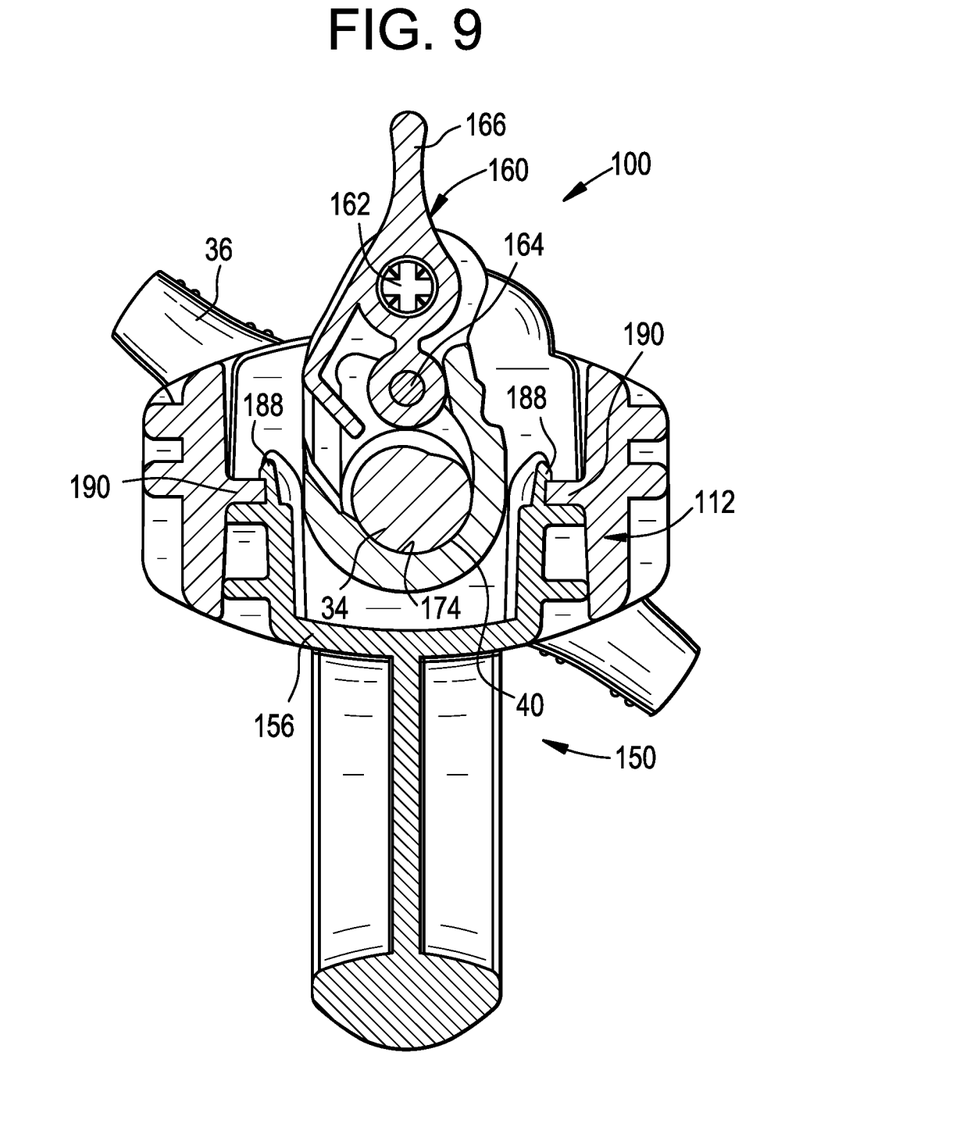
FIGS. 9 and 10 are cross-sectional views of the fluid displacement and pressurizing device shown in FIGS. 6-7, taken along line B-B of FIG. 6, showing the device in two different states.

Preferably, the housing 112 and carrier member 150 are configured such that the carrier member 150 snaps in place in the carrier receptacle 146. To this end, as shown in FIGS. 7, 8 and 9, the housing 112 may include striker bar elements 190 which are configured to engage latch elements 188 on the carrier member 156. The carrier sub-assembly 150 will now be described.

The preferred components of the carrier sub-assembly 150 of the device 100 shown in FIGS. 6 and 7 can best be seen in FIG. 8, which provides an exploded view of the carrier sub-assembly 150. As shown in FIG. 8, the carrier sub-assembly 150, much like the carrier sub-assembly 50 shown in FIG. 3, preferably comprises a carrier member 156, a plunger engaging member such as a nut member or specifically a half nut 158, and an actuating lever-link member 160. The actuating lever-link member 160 is coupled to the half nut 158 via a first pivot pin 162, and is coupled to the carrier member 156 via a second pivot pin 164. All the components may be formed of plastic, but the second pivot pin may instead be formed of metal.

Figure 10:
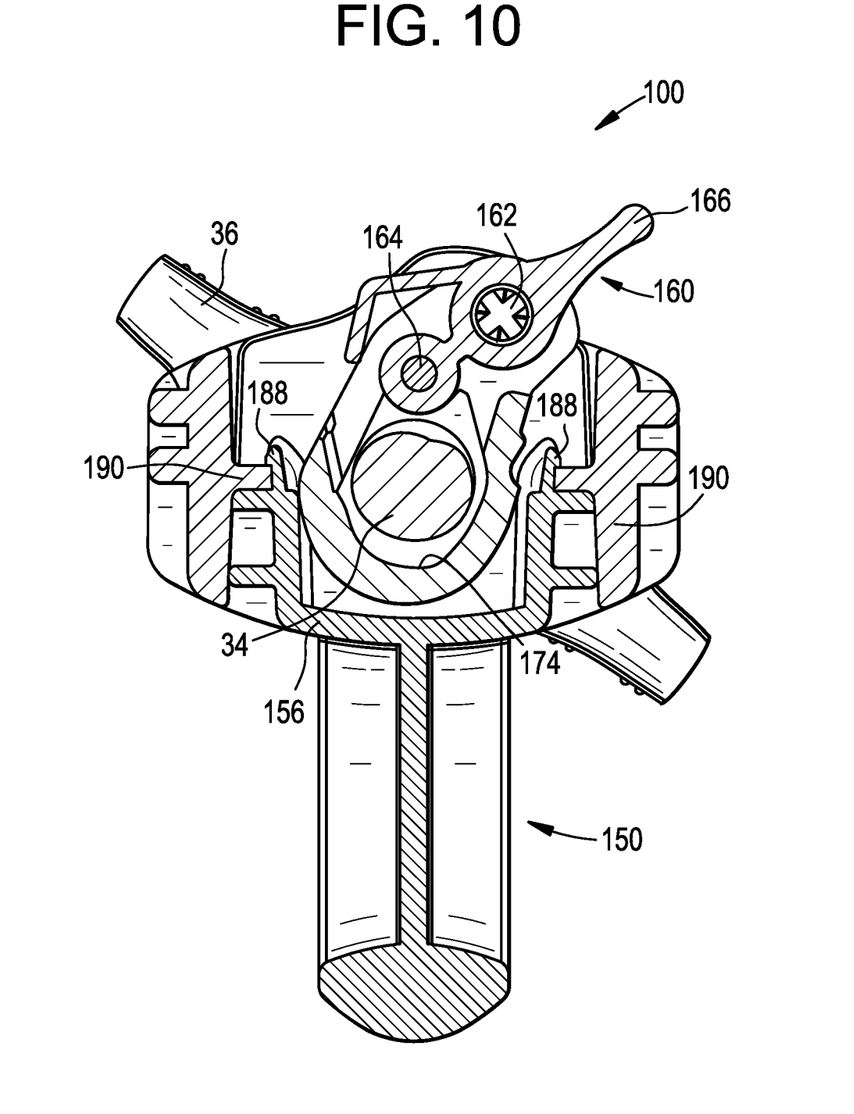

Preferably, the actuating lever-link member 160 includes a control surface 166, a receptacle 168 through which the first pivot pin 162 extends, and a bearing 170 through which the second pivot pin 164 extends. Preferably, the nut member 158 includes an opening 176 through which the plunger 34 extends, bearings 172 for retaining the first pivot pin 162, and thread segments 174. The carrier member 156 provides a handle portion 187, as well as preferably includes receptacles 184 (i.e., one at each end) through which the plunger 34 extends, and receptacles 182 for retaining the second pivot pin 164. Preferably, as shown best in FIGS. 9 and 10, the carrier member 156 also includes latch elements 188 which engage the striker bar elements 190 inside the housing 112, thereby effectively locking the carrier sub-assembly 150 in place.

With regard to the structure and function of the half nut 158 and the actuating link-lever 160, such as when the control surface 166 of the actuating link-lever 160 is pressed or released, or when the handle 36 of the plunger 34 is pushed, pulled or rotated, this need not be explained in extreme detail herein, as that detail is fully explained in the patents previously-identified herein.

With regard to assembly of the device 100 shown in FIGS. 6 and 7, first the carrier sub-assembly 150 is assembled, and then the carrier sub-assembly 150 is installed in the carrier receptacle 146 in the housing 112. To assemble the carrier sub-assembly 150, first the actuating lever-link member 160 is inserted into the half nut 158, and then the first pivot pin 162 is inserted into either one of the bearings 172 in the half nut 158, through the receptacle 168 in the lever-link member 160, and into the other bearing 172 in the half nut 158. This assembly is then engaged with the carrier member 156, aligning the bearing 170 of the actuating lever-link 160 with the receptacles 182 in the carrier member 156. The second pivot pin 164 is then inserted into either one of the receptacles 182, through the bearing 170 in the actuating lever-link 160, and into the other receptacle 182 in the carrier member 156, thereby securing all parts of the carrier sub-assembly 150 into working alignment.

Either before or after assembling the carrier sub-assembly 150, the piston 22 (along with the sealing member 24 thereon) is inserted into the barrel 114 of the housing 112, thereby causing the sealing member 24 to seal with an internal wall in the barrel 114 of the housing 112.

Regardless, after the piston 22 has been installed in the barrel 114, and after the carrier sub-assembly 150 has been assembled, the carrier sub-assembly 150 is then installed into the carrier receptacle 146 in the housing 112. This installation is performed in a direction which is traverse to the longitudinal axis 152 of the housing 112 (the direction of installation is shown using arrow 154 in FIG. 7), causing the deflectable latch elements 188 to slide past and snap into retaining engagement with the striker bar elements 190 which are provided in the housing 112 (see FIGS. 9 and 10), thereby securing the carrier sub-assembly 150 in the housing 112.

After the carrier sub-assembly 150 is installed relative to the housing 112, the end 32 of the plunger 34 is engaged with the piston 22. To do this, the control surface 166 of the actuating link-lever 160 is pressed which causes the half nut 158 to de-actuate and shift, thereby effectively clearing a passageway for the end 32 of the plunger 34 to access the piston 22. To engage the end 32 of the plunger 34 with the piston 22, while the control surface 166 is being pressed, the end 32 of the plunger 34 is inserted into the end 194 of the housing 112, into one of the receptacles 184 in the carrier member 156, pushed through the half nut 158 (i.e., into opening 177), through the other receptacle 184 in the carrier, and into secure mating engagement with the piston 22 which is in the barrel 114. Thereafter, the control surface 166 can be released, causing the half nut 158 to pivot into threaded engagement with the plunger 34. At this point (assuming a delivery line is engaged with the outlet port 119), the device is ready for operation.

With regard to operation of the device 100 after it has been assembled, while holding the device by handle 187 with one hand, the user's other hand can interact with both the control surface 166 and the handle 36 of the plunger 34, both regard to macro movement and micro movement of the plunger 34, are disclosed in detail the previously-identified patents, and need not be repeated in extreme detail here. That being said, generally speaking, the actuating lever-link 160 is configured such that the actuating lever-link 160 biases the half nut 158 into threaded engagement with the thread 40 of the plunger 34 (see FIG. 9). At this time, the handle 36 of the plunger 34 is rotatable to cause micro-movement of the plunger 34 (and the piston 22 thereon). Pressing the control surface 166 of the actuating lever-link 160 causes the half nut 158 to disengage from the thread 40 on the plunger 34 (see FIG. 10), thereby allowing macro-movement of the plunger 34 (and the piston 22 thereon) by pushing or pulling on the handle 36.

Both devices (i.e., the inflator shown in FIGS. 1-2 and the orthopedic cement delivery device shown in FIG. 6-7) provide that a fully assembled carrier sub-assembly gets installed in a housing in a direction which is traverse to a longitudinal axis of the housing. This provides for easy manual assembly, as well as greatly facilitates automating the assembly process. The transversely snap-in carrier approach disclosed herein allows construction of a relatively inexpensive, highly loaded, ultra-high pressure device within a reasonably compact structure while providing necessary handle surfaces for interaction by a user.

The transversely snapped in carrier sub-assemblies disclosed herein solve several problems encountered with high capacity and ultra-high pressure polymeric inflation and delivery device designs. Either carrier sub-assembly is installed by inserting the sub-assembly straight into the housing, transversely to a longitudinal axis of the housing, which simplifies manufacturing for automated assembly and reduced cost. Integral handle and gripping features make control and operation of the devices easier for users, and allows the carrier member to resolve torsional operating loads within itself to prevent torsional loads from reaching the device body. The snap-in retaining features that hold the carrier member of each device in place need not be designed to resist torsional loading during use. The carrier sub-assemblies provide greater surface area to distribute and transfer longitudinal, plunger divided loads, directly to the device body's receiving structure during pressurization. Having more surface area to distribute the carrier's load upon the housing allows use of lower strength specialized polymers and in some instances, lower cost polymer materials in the bodies of extremely high performance, high pressure syringe applications.

While specific embodiments of the invention have been shown and described, it is envisioned that those skilled in the art may devise various modifications without departing from the spirit and scope of the present invention.

What is claimed is:

1. A fluid displacement and pressurizing device comprising: a housing having a longitudinal axis; and a carrier member which is disposed generally in the housing, and which is removable from the housing; a plunger which extends through the carrier member; a plunger engaging structure pinned to, and moveable relative to, the carrier member, wherein the plunger engaging structure is selectively engageable with, and disengageable from, the plunger, wherein the housing and the carrier member are configured such that the carrier member and the plunger engaging structure are transversely installable in the housing relative to the longitudinal axis of the housing after the plunger engaging structure has been pinned to the carrier member.

2. The fluid displacement and pressurizing device as recited in claim 1, wherein the housing comprises a carrier receptacle which is configured to receive the carrier member, wherein the carrier receptacle and carrier member are configured such that the carrier member is installable into the carrier receptacle in a direction which is traverse to the longitudinal axis of the housing.

3. The fluid displacement and pressurizing device as recited in claim 1, wherein both the carrier member and the plunger engaging structure form a sub-assembly, and the sub-assembly is transversely installable in the housing after having been assembled.

4. The fluid displacement and pressurizing device as recited in claim 3, wherein the housing comprises a carrier receptacle which is configured to receive the sub-assembly, wherein the housing and sub-assembly are configured such that the sub-assembly is installable relative to the housing in a direction which is traverse to the longitudinal axis of the housing.

5. The fluid displacement and pressurizing device as recited in claim 1, wherein the plunger engaging structure comprises a nut member and an actuating lever-link member, wherein the actuating lever-link member is coupled to the nut member, and the actuating lever-link member is coupled to the carrier member.

6. The fluid displacement and pressurizing device as recited in claim 5, wherein the actuating lever-link member is coupled to the nut member via a first pivot pin, and the actuating lever-link member is coupled to the carrier member via a second pivot pin.

7. The fluid displacement and pressurizing device as recited in claim 6, wherein the actuating lever-link member comprises a control surface, wherein the actuating lever-link member provides a receptacle for receiving the first pivot pin, and wherein the actuating lever-link member provides a bearing for receiving the second pivot pin.

8. The fluid displacement and pressurizing device as recited in claim 6, wherein the nut member comprises bearings for receiving the first pivot pin, thread segments on an inner surface of the nut member for selective engagement with the plunger, and an opening in the nut member through which the plunger extends.

9. The fluid displacement and pressurizing device as recited in claim 6, wherein the actuating lever-link member is coupled to the nut member via the first pivot pin, wherein the first pivot pin extends through the receptacle in the actuating lever-link member, and is retained proximate each of its ends by the bearings of the nut member.

10. The fluid displacement and pressurizing device as recited in claim 6, wherein the carrier member has spaced-apart walls which define a pocket for receiving the nut member and the actuating lever-link member, wherein the carrier member comprises receptacles for receiving the second pivot pin, openings which define a plunger passageway through which the plunger extends, and handle portions, wherein the nut member and the actuating lever-link member are coupled to the carrier member via the second pivot pin, wherein the second pivot pin extends through the bearing in the actuating lever-link member, and is retained by the receptacles in the carrier member.

11. The fluid displacement and pressurizing device as recited in claim 1, wherein the housing and the carrier member are configured such that the carrier member snaps in place relative to the housing.

12. The fluid displacement and pressurizing device as recited in claim 1, wherein the carrier member comprises deflectable latch elements which engage striker bar elements which are provided in the housing, proximate the carrier receptacle, thereby securing the carrier member in the housing.

13. The fluid displacement and pressurizing device as recited in claim 1, wherein the carrier member provides a handle portion, as well as provides receptacles through which the plunger extends.

* * * * *